(12) United States Patent
Akagane

(10) Patent No.: US 11,253,286 B2
(45) Date of Patent: Feb. 22, 2022

(54) SURGICAL TREATMENT DEVICE

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 261 days.

(21) Appl. No.: 16/282,653

(22) Filed: Feb. 22, 2019

(65) Prior Publication Data

US 2019/0183522 A1 Jun. 20, 2019

Related U.S. Application Data

(63) Continuation of application No. PCT/JP2016/074509, filed on Aug. 23, 2016.

(51) Int. Cl.
| | | |
|---|---|---|
| *A61B 17/28* | (2006.01) | |
| *A61B 17/32* | (2006.01) | |
| *A61B 17/00* | (2006.01) | |
| *A61B 17/295* | (2006.01) | |
| *A61B 18/00* | (2006.01) | |

(52) U.S. Cl.
CPC ...... *A61B 17/320092* (2013.01); *A61B 17/00* (2013.01); *A61B 17/295* (2013.01); *A61B 2017/320094* (2017.08); *A61B 2018/00101* (2013.01); *A61B 2018/00107* (2013.01); *A61B 2018/00994* (2013.01)

(58) Field of Classification Search
CPC ............ A61B 17/320092; A61B 17/00; A61B 17/295; A61B 2017/320094; A61B 2018/00101; A61B 2018/00107; A61B 2018/00994
See application file for complete search history.

(56) References Cited

U.S. PATENT DOCUMENTS

| | | | |
|---|---|---|---|
| 5,752,965 A * | 5/1998 | Francis | A61B 17/07207 227/178.1 |
| 6,325,811 B1 * | 12/2001 | Messerly | A61B 17/320092 606/169 |
| 2002/0082556 A1 * | 6/2002 | Cioanta | A61B 18/04 604/113 |

(Continued)

FOREIGN PATENT DOCUMENTS

| | | |
|---|---|---|
| JP | H10-314178 A | 12/1998 |
| JP | 2008-200922 A | 9/2008 |

(Continued)

OTHER PUBLICATIONS

Nov. 22, 2016 International Search Report issued in International Patent Application No. PCT/JP2016/074509.

(Continued)

*Primary Examiner* — Erich G Herbermann
(74) *Attorney, Agent, or Firm* — Oliff PLC

(57) ABSTRACT

A surgical treatment device includes: a treatment portion including a treatment surface that treats biological tissue by supplying at least one type of energy; a heat insulation coating that covers at least a part of an outer surface of the treatment portion; and a protection coating that is provided in a manner to cover the heat insulation coating and is higher in coating strength than the heat insulation coating.

20 Claims, 4 Drawing Sheets

(56) References Cited

U.S. PATENT DOCUMENTS

| | | | |
|---|---|---|---|
| 2008/0281316 A1* | 11/2008 | Carlton | A61B 18/1445 606/40 |
| 2013/0303949 A1* | 11/2013 | Kawaguchi | A61B 17/282 601/2 |
| 2015/0148835 A1 | 5/2015 | Faller et al. | |
| 2015/0297289 A1 | 10/2015 | Hirai et al. | |

FOREIGN PATENT DOCUMENTS

| | | |
|---|---|---|
| JP | 2011-505198 A | 2/2011 |
| JP | 5866486 B2 | 2/2016 |

OTHER PUBLICATIONS

Feb. 26, 2019 International Preliminary Report on Patentability issued in International Application No. PCT/JP2016/074509.

* cited by examiner

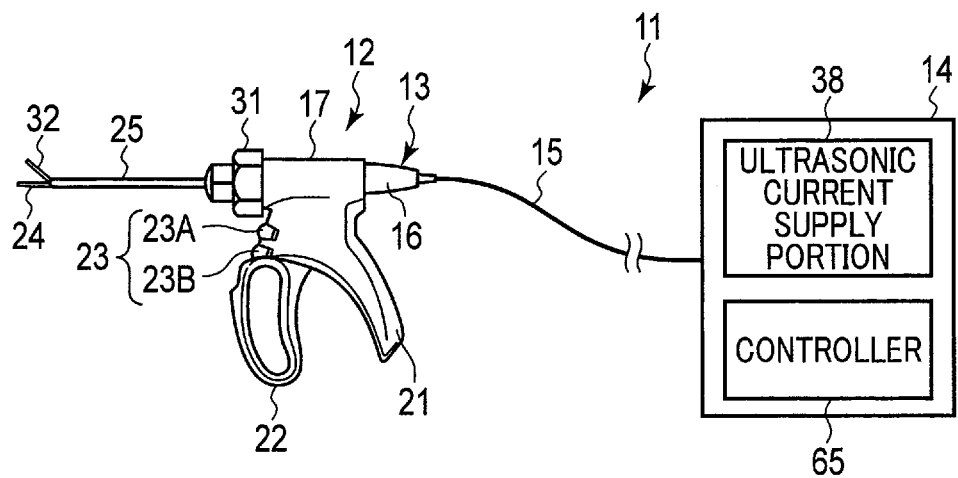
F I G. 1
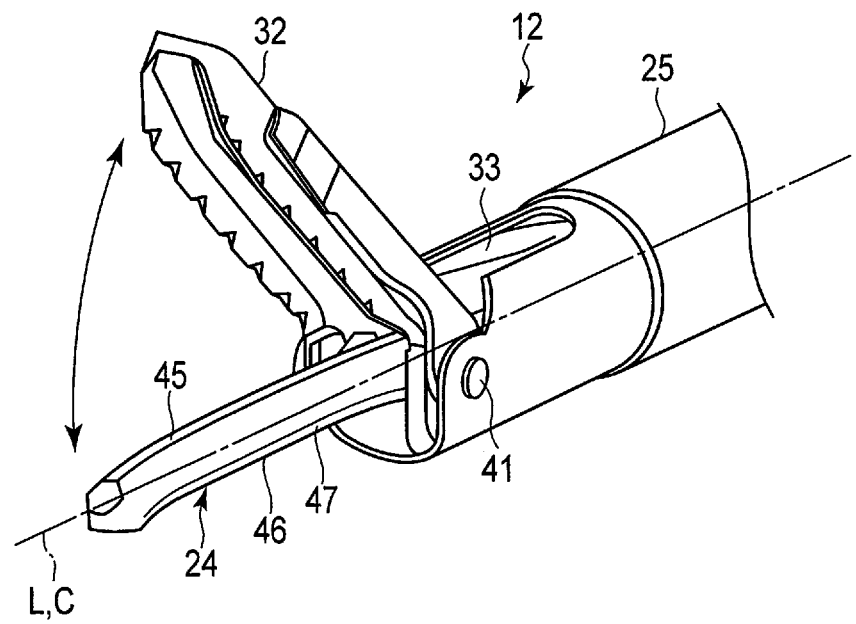
F I G. 2

SURGICAL TREATMENT DEVICE

CROSS-REFERENCE TO RELATED APPLICATIONS

This application is a Continuation Application of PCT Application No. PCT/JP2016/074509, filed Aug. 23, 2016, the entire contents of all of which are incorporated herein by reference.

FIELD

The present invention relates to a surgical treatment device that treats body tissue with energy.

BACKGROUND

Jpn. PCT National Publication No. 2011-505198 discloses an ultrasonic scalpel and an electrosurgical device. This ultrasonic scalpel is vibrated at a high frequency (for example, 55,500 times per second) to denature protein in tissue. Furthermore, a blood vessel is squashed by the combination of a pressure applied by a blade surface to tissue, and a clamping mechanism, so that a coagulum forms a hemostatic seal.

Jpn. Pat. Appln. KOKAI Publication No. 10-314178 discloses a pair of surgical scissor-type forceps. This pair of surgical scissor-type forceps includes a scissor portion and a grip portion, and severs biological tissue with the scissor portion while the biological tissue is held by the grip portion.

SUMMARY

A surgical treatment device according to one aspect of the present invention comprises: a treatment portion including a treatment surface that treats biological tissue; a heat insulation coating that forms a part of an outer surface of the treatment portion and covers a part other than the treatment surface; and a protection coating that is covered in a manner to cover the heat insulation coating in the part other than the treatment surface and is higher in coating strength than the heat insulation coating.

BRIEF DESCRIPTION OF THE DRAWINGS

FIG. 1 is a schematic diagram showing the entire configuration of a surgical treatment device according to the first embodiment.

FIG. 2 is a perspective view showing a distal portion of a probe and a jaw of a handpiece in the surgical treatment device shown in FIG. 1.

DETAILED DESCRIPTION

First Embodiment

A first embodiment of a surgical treatment device according to the present invention will be described with reference to FIG. 1 to FIG. 7.

Figure 3:
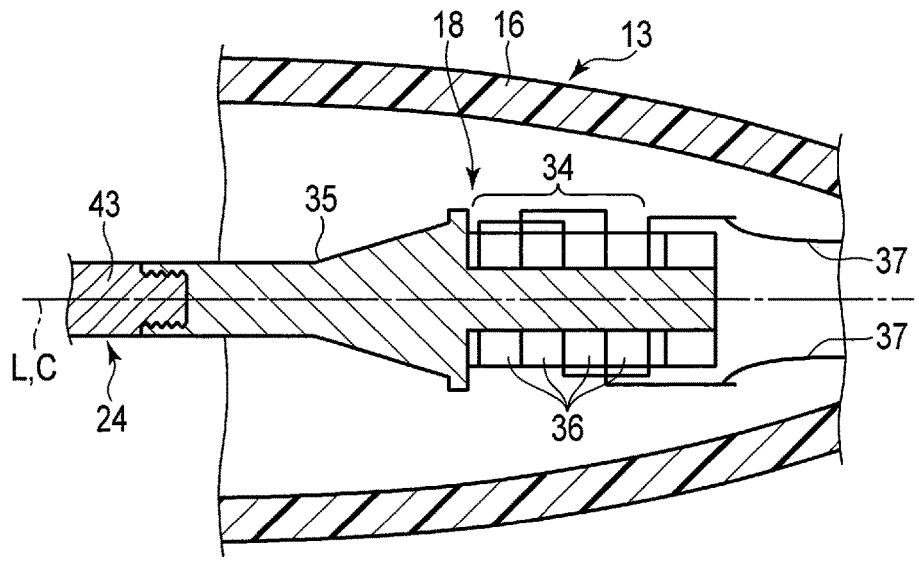
FIG. 3 is a cross-sectional view showing a vibrator unit in the surgical treatment device shown in FIG. 1.

As shown in FIG. 1, a surgical treatment device 11 includes a handpiece 12, a vibrator unit 13 that is detachably attachable with respect to the handpiece 12, a power source unit 14, and a cable 15 that connects the handpiece 12 and the power source unit 14. As shown in FIG. 3, the vibrator unit 13 includes a case 16 and a vibration generator 18 (transducer) housed in the case 16 that is detachably attachable with respect to a housing 17.

As shown in FIG. 1 to FIG. 5, the handpiece 12 includes: the housing 17 that forms an outer shell; a fixed handle 21 that is provided integrally with the housing 17; a handle 22 that is rotatable with respect to the housing 17; a plurality of operation buttons 23 that are provided in the housing 17; a rod-shaped probe 24 (treatment portion, an ultrasonic probe) that is connected to the vibration generator 18; a cylindrically-shaped shaft 25 that covers the periphery of the probe (rod member) 24 in its proximal side to protect the probe 24; a heat insulation coating 26 that covers a part of the outer surface of, the probe 24; a protection coating 27 provided in a manner to cover the heat insulation coating 26; a ring-shaped supporter 28 (lining) that has electrical insulation properties, such as rubber, and is provided between the probe 24 and the shaft 25; a knob for rotation (hereinafter, referred to as a rotation knob) 31 that is fixed to the shaft 25; a jaw 32 that is provided in a manner to be rotatable with respect to the probe 24 and the shaft 25; and a cylindrically-shaped advance-and-retreat portion 33 that is provided inside the shaft 25 and is caused to advance or retreat when the jaw 32 is opened or closed. In the present embodiment, one of the two directions parallel to a longitudinal direction L of the probe 24 is defined as a distal side, and the other direction opposite to the distal side is defined as a proximal side. The longitudinal direction L extends along a central axis C of the probe 24.

As shown in FIG. 3, the vibration generator 18 includes an ultrasonic vibrator 34 and a horn member 35. The ultrasonic vibrator 34 is provided with a plurality of piezoelectric elements 36 (for example, four piezoelectric elements 36, in the present embodiment) that convert current into ultrasonic vibration. The ultrasonic vibrator 34 is connected to one end of an electric wire 37. The electric wire 37 extends through the inside of the cable 15, and is connected to an ultrasonic current supply portion 38 in the power source unit 14 at the other end. When electric power is supplied from the ultrasonic current supply portion to the ultrasonic vibrator 34 via the electric wire 37, ultrasonic vibration is generated in the ultrasonic vibrator 34.

As shown in FIG. 3, the ultrasonic vibrator 34 is attached to the horn member 35. The horn member 35 is made of a metal material, for example. The horn member 35 has a substantially conically shaped cross-section change portion that decreases in cross section towards the distal side of the probe 24. Ultrasonic vibration generated in the ultrasonic vibrator 34 is so-called longitudinal vibration, and a vibration direction of this vibration corresponds to the longitudinal direction L of the probe 24. The amplitude of the ultrasonic vibration is expanded in the cross-section change portion of the horn member 35.

Figure 4:
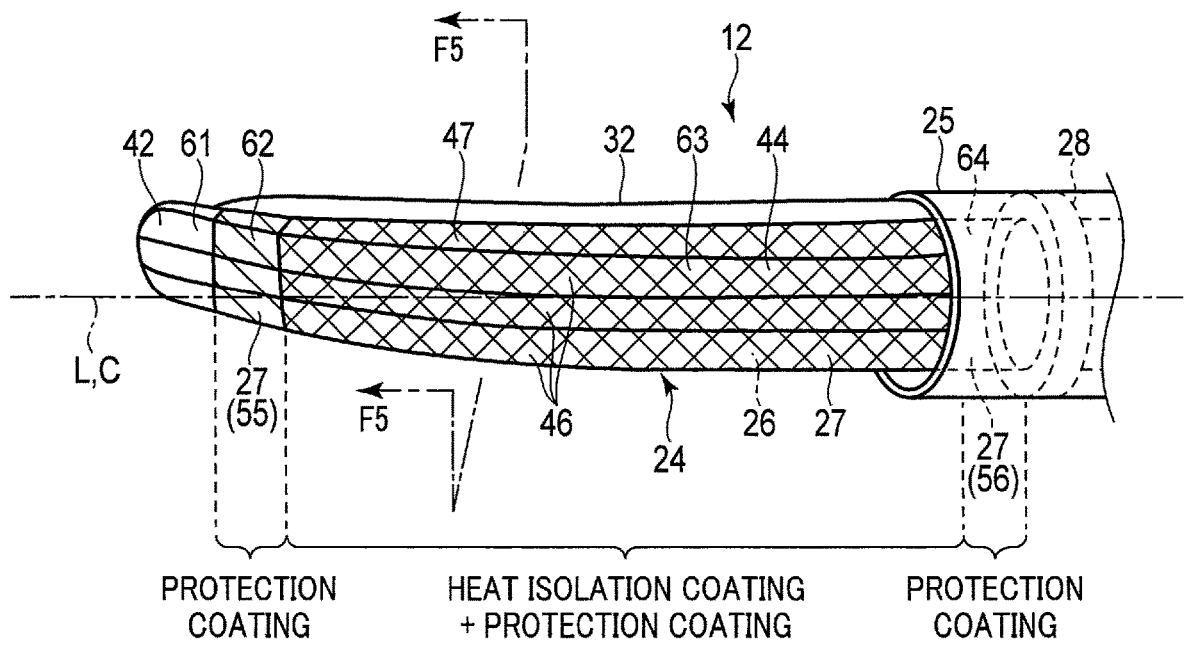
FIG. 4 is a perspective view showing a region in which a heat insulation coating and a protection coating that are provided in the probe show in FIG. 2 are formed.

As shown in FIG. 4, the supporter 28 is provided in a node position of the ultrasonic vibration generated by the vibration generator 18, or in the vicinity of the node position. The supporter 28 supports the probe 24 and seals the inside of the shaft 25 so as to prevent fluid or fragments of treated biological tissue from entering through the supporter 28 towards the proximal side.

As shown in FIG. 2 and FIG. 4, the shaft 25 is formed in a cylindrical shape and protects the probe 24 placed inside the shaft 25. The shaft 25 is attached to the housing 17 rotatably with respect to the housing 17, on the proximal side. The rotation knob 31 is provided to be fixed to the shaft 25. By rotating the rotation knob 31 with respect to the housing 17, the shaft 25, the probe 24, the ultrasonic vibrator 34, and the jaw 32 can be rotated integrally around the central axis C. The shaft 25 includes a support pin 41 for supporting the jaw 32 in the distal portion 42.

As indicated by the arrow in FIG. 2, the jaw 32 is rotatable about the support pin 41 between a facing position where the jaw 32 faces the probe 24 and a separate position where the jaw 32 is separate from the probe 24. An operator can open and close the jaw 32 by rotating the handle 22 with respect to the housing 17. That is, when an operator operates the handle 22, the advance-and-retreat portion 33 provided inside the shaft 25 advances or retreats along the central axis C of the shaft 25, thereby opening or closing the jaw 32.

Figure 5:
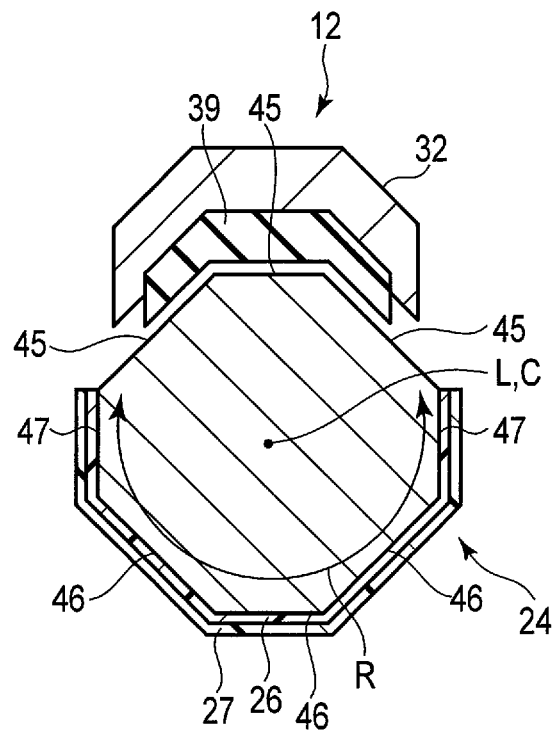
FIG. 5 is a cross-sectional view taken along line F5-F5 of the probe, the jaw, the heat insulation coating, and the protection coating shown in FIG. 4.

As shown in FIG. 4, the probe 24 (treatment portion) is made of, for example, a biocompatible metal material (e.g., a titanium alloy) in a rod-like shape that is curved in a manner such that the distal side of the probe 24 is laterally displaced with respect to the central axis C. An ultrasonic vibration (ultrasonic energy) that is transmitted to the probe 24 enables the probe 24 to treat biological tissue. The probe 24 includes, in its longitudinal direction L, the distal portion 42 located on the distal side, a proximal portion 43 (see FIG. 3) on the side opposite to the distal portion 42, and an intermediate portion 44 provided in a position between the distal portion 42 and the proximal portion 43. As shown in FIG. 5, the probe 24 includes, in a circumferential direction R, a treatment surface 45 for performing treatment such as coagulation treatment or coagulation-and-incision treatment with respect to biological tissue, and an opposite surface 46 on the side opposite to the treatment surface 45.

The probe 24 includes the treatment surface 45 that treats biological tissue. The probe 24 is formed in a manner such that its cross-sectional shape forms an octagon, in which, for example, three surfaces that face the jaw 32 constitute the treatment surface 45, while three surfaces that face the treatment surface 45 constitute the opposite surface 46. A pair of side surfaces 47 is provided between the treatment surface 45 and the opposite surface 46. In the jaw 32, a position facing the treatment surface 45 is provided with a pad 39 made of a resin material having an electrical insulation property as well as heat resistance and wear resistance, such as a PTFE material, for example. In the case where the jaw 32 and the probe 24 are positioned to face each other, the treatment surface 45 may come in contact with the pad 39.

Figure 6:
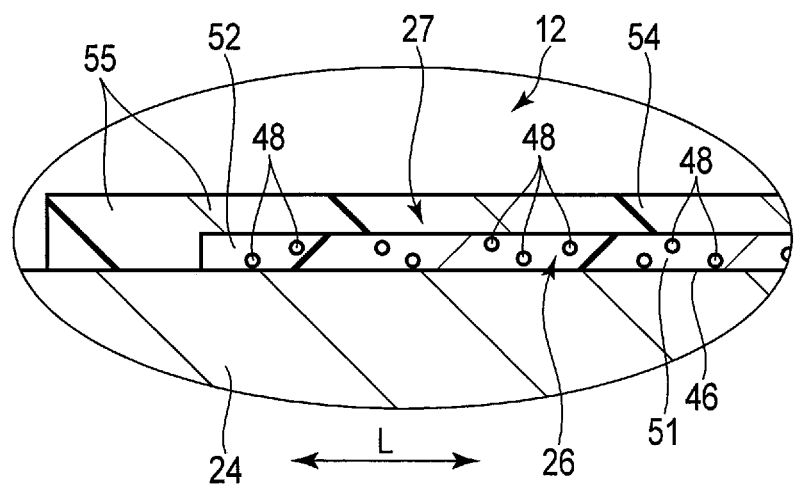
FIG. 6 is a cross-sectional view obtained by cutting the probe, the heat insulation coating, and the protection coating, in the vicinity of a distal portion of the probe shown in FIG. 4, along the surface extending in longitudinal direction.
Figure 7:
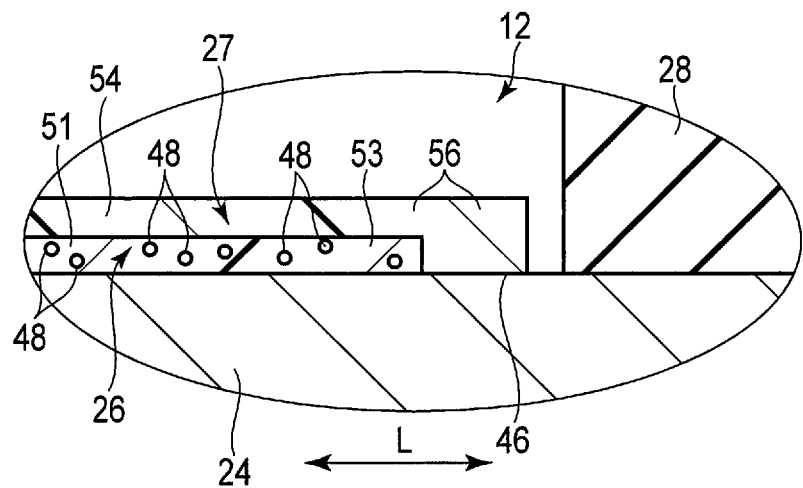
FIG. 7 is a cross-sectional view obtained by cutting the probe, the heat insulation coating, and the protection coating in the vicinity of a center portion (a support) of the probe shown in FIG. 4, along the surface extending in the longitudinal direction.

The heat insulation coating 26 is formed in a manner to have an appropriate thickness within a range from, for example, several μm to several hundred μm, in accordance with an internal organ, an organ, or tissue, as a treatment target. The heat insulation coating 26 as a whole includes a porous configuration. As shown in FIG. 6 and FIG. 7, the heat insulation coating 26 is formed by dispersively mixing particles 48 (hollow particles) having a heat insulation property, into a base material made of, e.g., a PEEK resin. A material for the base member of the heat insulation coating 26 may be a resin material other than PEEK. Each of the particles 48 is made of hollow spherical glass (soda lime borosilicate glass), silica (silicone dioxide), etc. However, the particles 48 may be made of other materials. Each of the particles 48 contains therein a space filled with air. This enables the particles 48 to exhibit a heat insulation property. The particles 48 are not constant in diameter, and the particles 48 with various particle diameters are mixed together. However, all diameters of the particles 48 are smaller than the thickness of the heat insulation coating 26. The particles 48 are not limited to a spherical shape, and may be formed in various shapes such as an oval spherical shape and a thin scale-like shape.

The heat insulation coating 26 includes, in the longitudinal direction L of the probe 24, a main body portion 51, a first end 52 provided in the distal side, and a second end 53 provided on the side opposite to the first end 52. The heat insulation coating 26 covers a part other than the distal portion 42 of the probe 24. That is, the first end 52 is formed in a position closer to the proximal side than the distal portion 42 of the probe 24. In other words, the first end 52 is provided in a position displaced from the distal portion 42 of the probe 24. The second end 53 is provided in the vicinity of the supporter 28 in a manner to be closer to the distal side than the supporter 28. As shown in FIG. 5, the heat insulation coating 26 is provided across the opposite surface 46 and the pair of side surfaces 47 in the circumferential direction R of the probe 24. The heat insulation coating 26 covers a part other than the treatment surface 45.

In the heat insulation coating 26, heat conducted from the probe 24 is conducted to the outside through paths around the particles 48. Therefore, in the thickness direction of the heat insulation coating 26, a distance in which heat is conducted in the heat isolation coating 26 is larger than the actual thickness of the heat insulation coating 26. Thus, in the heat insulation coating 26, the heat flux (the amount of heat conducted per unit time) in the cut-through direction of the heat insulation coating 26 is reduced.

The protection coating 27 is formed in a manner to have an appropriate thickness within a range from, for example, several μm to several hundred μm, in accordance with an internal organ, an organ, or tissue, as a treatment target. The protection coating 27 is made of a resin material such as PEEK. However, the protection coating 27 may be made of a resin other than PEEK. The protection coating 27 is provided in a part other than the treatment surface 45 in a manner to cover the probe 24 and the heat insulation coating 26. The protection coating 27 is higher in coating strength than the heat insulation coating 26. As shown in FIG. 4, FIG. 6, and FIG. 7, the protection coating 27 includes, in the longitudinal direction L of the probe 24, a protection coating main body 54, a first part 55 provided in the distal side, and a second part 56 provided in the proximal side on the side opposite to the distal portion 42. The protection coating 27 does not contain the particles 48 that exhibit a heat insulation property.

As shown in FIG. 4, the protection coating 27 is longer in the longitudinal direction L than the heat insulation coating 26. That is, the probe 24 is provided with: in the longitudinal direction L, a distal region 61 (distal portion 42) in which no coating is formed; a quasi-distal region 62 that is provided closer to the proximal side than the distal portion 42 and is provided with the first part 55 of the protection coating 27; an intermediate region 63 that is provided closer to the proximal side than the quasi-distal region 62 and is provided with the heat insulation coating 26 and the protection coating 27; and a proximal end region 64 that is provided closer to the proximal side than the intermediate region 63 and is provided with the second part 56 of the protection coating 27.

As shown in FIG. 6, the first part 55 of the protection coating 27 seals the first end 52 of the heat insulation coating 26 on the distal side. As shown in FIG. 7, the second part 56 of the protection coating 27 seals the second end 53 of the heat insulation coating 26 on the proximal side in a position closer to the distal side than the supporter 28. On the other hand, as shown in FIG. 5, the protection coating 27 is provided across the opposite surface 46 and the pair of side surfaces 47 in the circumferential direction R of the probe 24. Similarly, the heat insulation coating 26 is provided across the opposite surface 46 and the pair of side surfaces 47 in the circumferential direction R of the probe 24. That is, the protection coating 27 and the heat insulation coating 26 are formed to be equal in width in the circumferential direction R.

The protection coating 27 and the heat insulation coating 26 are formed through the following steps, for example. A resin as a material for the heat insulation coating 26 is applied to the probe 24, so that the heat insulation coating 26 is formed through a preliminary baking step performed at a comparatively low temperature and a main baking step performed at a comparatively high temperature. A resin as a material for the protection coating 27 is applied to the surface of this heat insulation coating 26 and its circumference, so that the protection coating 27 is formed through a preliminary baking step performed at a comparatively low temperature and a main baking step performed at a comparatively high temperature. This results in the formation of a composite coating in which the upper side of the heat insulation coating 26 is coated with the protection coating 27.

As shown in FIG. 1, the power source unit 14 includes the ultrasonic current supply portion 38 and the controller 65 that controls the ultrasonic current supply portion 38. The controller 65 can control supply of electric power from the ultrasonic current supply portion 38 to the ultrasonic vibrator 34. When an operator operates the operation buttons 23, the controller 65 supplies current from the ultrasonic current supply portion 38 to the vibration generator 18.

The plurality of operation buttons 23 include a first operation button 23A corresponding to a coagulation mode and a second operation button 23B corresponding to a coagulation-and-incision mode. Therefore, for example, when an operator operates the first operation button 23A, the probe 24 outputs ultrasonic energy suitable for coagulation of biological tissue under control of the aforementioned controller 65. For example, when an operator operates the second operation button 23B, the probe 24 outputs ultrasonic energy suitable for coagulation and incision of biological tissue under control of the aforementioned controller 65.

Hereinafter, the operation of the surgical treatment device 11 according to the present embodiment will be described with reference to FIG. 4 to FIG. 7.

During treatment, an operator can sandwich biological tissue between the probe 24 and the jaw 32 by operating the handle 22. Furthermore, an operator can perform coagulation-and-incision treatment or only coagulation treatment by operating the first operation button 23A or the second operation button 23B to thereby input ultrasonic energy to the sandwiched biological tissue.

When a coagulation-and-incision treatment or coagulation treatment is performed for a long time, the probe 24 may reach a high temperature over 200 degrees Celsius, for example. In the present embodiment, the heat insulation coating 26 and the protection coating 27 are provided in the opposite surface 46 on the side opposite to the treatment surface 45 of the probe 24. Accordingly, by the heat insulation action of the heat insulation coating 26, the amount of heat that is conducted to the surface of the protection coating 27 per unit time is maintained small. Therefore, the temperature of the surface of the protection coating 27 is maintained extremely low as compared to the treatment surface 45. With this configuration, while performing treatment, even if an operator unintentionally brings the opposite surface 46 side of the probe 24 in contact with ambient tissue around a treatment target, the ambient tissue can be prevented from being damaged by heat from the probe 24.

When the probe 24 is ultrasonically vibrated in fluid, cavitation is prone to occur in the distal portion 42 of the probe 24. In the present embodiment, the heat insulation coating 26 and the protection coating 27 are provided in a position displaced from the distal portion 42 in which cavitation is prone to occur, so that the heat insulation coating 26 and the protection coating 27 are prevented to the greatest extent possible from being dropped out of the probe 24.

Furthermore, the first end 52 and the second end 53 of the heat insulation coating 26 are sealed with the protection coating 27 in the longitudinal direction L of the probe 24. This prevents the heat insulation coating 26 from being peeled off at the first end 52 and the second end 53.

According to the first embodiment, the surgical treatment device 11 is configured as follows. The surgical treatment device 11 includes: the probe 24 having the treatment surface 45 that treats biological tissue; the heat insulation coating 26 that forms a part of the outer surface of the probe 24 and covers a part other than the treatment surface 45; and the protection coating 27 that is provided in a manner to cover the heat insulation coating in a part other than the treatment surface 45 and is higher in coating strength than the heat insulation coating 26.

According to this configuration, the formation of the heat insulation coating 26 makes it hard for heat of the probe 24 to be conducted to a part other than the treatment surface 45. With this configuration, while performing treatment, even if an operator unintentionally brings any part except the treatment surface 45 in contact with ambient tissue around a treatment target, heat damage to the ambient tissue can be reduced. Accordingly, the surgical treatment device 11 with less thermal invasiveness can be provided. In addition, in order to secure a heat insulation property, the heat insulation coating 26 has a tendency to be lower in strength than general coatings. According to the above configuration, the heat insulation coating 26 can be protected with the protection coating 27 with high coating strength, so that the heat insulation coating 26 can be prevented from being dropped out of the probe 24.

The probe 24 is configured to treat the biological tissue with ultrasonic vibration, and the protection coating 27 is longer in the longitudinal direction L of the probe 24 than the heat insulation coating 26. This configuration enables the formation of the protection coating 27 having a sufficient length with respect to the heat insulation coating 26, so that the heat insulation coating 26 that has a strong tendency to be inferior in strength can be protected sufficiently with the protection coating 27. In addition, the heat insulation coating 26 makes it hard for the high temperature heat created by use of ultrasonic energy to be conducted to a part other than the treatment surface 45.

The heat insulation coating 26 and the protection coating 27 cover a part other than the distal portion 42 of the probe 24. According to this configuration, the heat insulation coating 26 and the protection coating 27 can be provided in a position displaced from the distal portion 42 in which cavitation is prone to occur at the time of ultrasonic vibration in a fluid. This prevents, to the greatest extent possible, the heat insulation coating 26 and the protection coating 27 from being peeled off from the probe 24 due to cavitation, so that a highly-durable surgical treatment device 11 can be provided.

The protection coating 27 seals the first end 52 provided on the distal portion 42 side of the heat insulation coating 26. According to this configuration, the first end 52 of the heat insulation coating 26 is protected with the protection coating 27, so that entry of fluid into the first end 52 is prevented to the greatest extent possible. This prevents peeling at the first end 52, so that a highly-durable surgical treatment device 11 can be provided.

The protection coating 27 seals the second end 53 provided on the side opposite to the distal portion 42 of the heat insulation coating 26. According to this configuration, the second end 53 of the heat insulation coating 26 is protected with the protection coating 27, so that entry of fluid into the second end 53 is prevented to the greatest extent possible. This prevents peeling at the second end 53, so that a highly-durable surgical treatment device 11 can be provided.

The heat insulation coating 26 contains the particles that exhibit a heat insulation property. According to this configuration, the heat insulation coating 26 can be further improved in heat insulation property. The decrease in strength caused by mixing of the particles 48 can be compensated by the strength of the protection coating 27, and the configuration in which the protection coating 27 and the heat insulation coating 26 are combined achieves a coating (composite coating) that has both a heat insulating property and a high coating strength.

Second Embodiment

Figure 8:
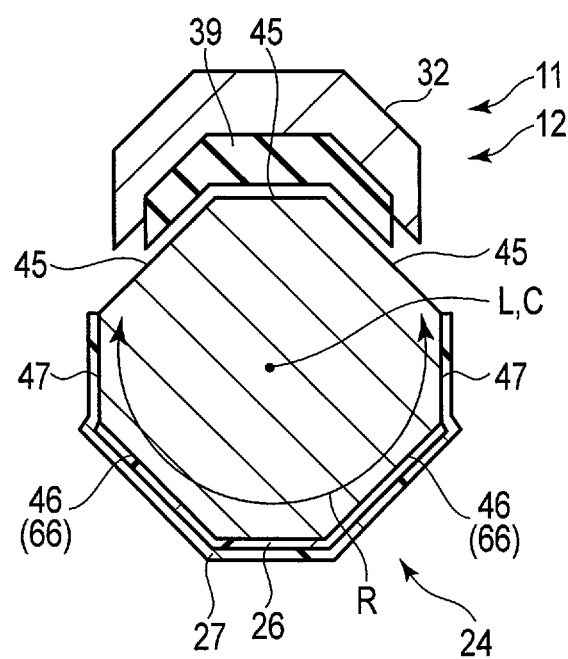
FIG. 8 is a cross-sectional view obtained by cutting a probe, a jaw, a heat insulation coating, and a protection coating of a surgical treatment device according to the second embodiment, along the same position as line F5-F5 shown in FIG. 4.

The surgical treatment device 11 according to a second embodiment will be described with reference to FIG. 8. The surgical treatment device 11 in the second embodiment differs from that in the first embodiment in terms of a width in which the heat insulation coating 26 is provided in the circumferential direction R of the probe 24 (treatment portion), but is the same as that in the first embodiment in terms of the other elements. Accordingly, the elements different from those in the first embodiment will be mainly explained, and description or illustration of the same elements as those in the first embodiment will be omitted.

In the present embodiment, the heat insulation coating is provided in the opposite surface 46 and is not provided in the pair of side surfaces 47 in the circumferential direction R of the probe 24. On the other hand, the protection coating 27 is provided across the opposite surface 46 and the pair of side surfaces 47. Therefore, the protection coating 27 is formed to be larger in width in the circumferential direction R than the heat insulation coating 26. Accordingly, in the present embodiment, the protection coating 27 seals both ends (inclined portions 66) of the heat insulation coating 26 in the circumferential direction R of the probe 24. The second embodiment is similar to the first embodiment in that the protection coating 27 seals the first end 52 and the second end 53 of the heat insulation coating 26 in the longitudinal direction L of the probe 24.

Subsequently, the operation of the surgical treatment device 11 according to the present embodiment will be described.

As in the first embodiment, an operator can perform coagulation-and-incision treatment or simply coagulation treatment by sandwiching biological tissue between the probe 24 and the jaw 32 to thereby input ultrasonic energy to the sandwiched biological tissue. When doing so, heat generated by the probe 24 is insulated by the heat insulation coating 26 on the opposite surface 46, thereby being hardly conducted to a part exposed to the outside. This can minimize damage caused to ambient tissue by heat of the probe 24 during treatment.

In the present embodiment, the both ends (inclined portions 66) of the heat insulation coating 26 are sealed with the protection coating 27 in the circumferential direction R of the probe 24 also, so that fluid does not enter in the circumferential direction R into the heat insulation coating 26, and peeling of the heat insulation coating 26 is prevented more surely.

According to the second embodiment, the protection coating 27 is larger in width in the circumferential direction R of the probe 24 than the heat insulation coating 26. According to this configuration, both ends of the heat insulation coating 26 in the circumferential direction R of the probe 24 can be sealed with the protection coating 27. This prevents fluid from entering in the circumferential direction R of the probe 24 into the heat insulation coating 26, and prevents the heat insulation coating 26 from peeling off from the probe 24, so that a highly-durable surgical treatment device 11 can be provided. Furthermore, the heat insulation coating 26 contains the particles 48 with a heat insulation property. Accordingly, the heat insulation coating 26 can be further improved in heat insulation property. The decrease in strength caused by mixing of the particles 48 can be compensated by the strength of the protection coating 27, and the configuration in which the protection coating 27 and the heat insulation coating 26 are combined achieves a coating (composite coating) that has both a heat insulating property and a high coating strength.

The present invention is not limited to the above-described embodiments, and can be appropriately modified in practice, without departing from the gist of the invention. Energy supplied to the probe 24 is not limited to ultrasonic energy and may be another form of energy. That is, ultrasonic energy, high frequency current energy, heat energy, light energy, and an electromagnetic wave may be output alone or in an appropriate combination.

For example, in the case where treatment is performed using high frequency current energy, physiological saline or the like can be prevented from entering into the heat insulation coating 26 through the protection coating 27. Therefore, ambient tissue can be prevented from being damaged by current flowing from the opposite surface 46 of the probe 24. Furthermore, a resin material such as a PEEK resin, which constitutes the heat insulation coating or the protection coating, generally has an electrical insulation property. This enables energization with high frequency current energy being focused on the treatment surface 45, so that efficient treatment is realized.

The invention claimed is:

1. A treatment device comprising:
   a treatment portion configured to treat biological tissue by supplying at least one type of energy;
   a heat insulating coating provided on the treatment portion; and
   a resin coating provided on the heat insulating coating and on the treatment portion, the resin coating being formed of a different material than the heat insulating coating, wherein the resin coating extends beyond both a distal end of the heat insulating coating and a proximal end of the heat insulating coating in a longitudinal direction of the treatment portion.

2. The treatment device according to claim 1, wherein the heat insulating coating and the resin coating are not provided in a distal-most region of the treatment portion.

3. The treatment device according to claim 1, wherein the resin coating extends beyond lateral sides of the heat insulating coating in a circumferential direction of the treatment portion.

4. The treatment device according to claim 1, wherein:
   the treatment portion includes:
      a treatment surface configured to treat the biological tissue, and
      an opposite surface on a side of the treatment portion opposite to the treatment surface; and
   the heat insulating coating is provided on at least a part of the opposite surface.

5. The treatment device according to claim 1, wherein the heat insulating coating has a porous structure.

6. The treatment device according to claim 1, wherein the resin coating has a higher coating strength than the heat insulating coating.

7. The treatment device according to claim 1, wherein the heat insulating coating includes a hollow particle having a heat insulation property.

8. The treatment device according to claim 1, wherein the resin coating does not contain a particle having a heat insulation property.

9. The treatment device according to claim 1, wherein the treatment portion is configured to treat the biological tissue with ultrasonic vibration.

10. The treatment device according to claim 1, wherein:
   the treatment portion includes a treatment surface configured to treat the biological tissue; and
   the resin coating and the heat insulating coating cover a part of the treatment portion other than the treatment surface.

11. The treatment device according to claim 1, wherein:
   the treatment portion is configured to treat the biological tissue with ultrasonic vibration; and
   the resin coating is longer in the longitudinal direction of the treatment portion than the heat insulating coating.

12. The treatment device according to claim 1, wherein the resin coating is wider in a circumferential direction of the treatment portion than the heat insulating coating.

13. The treatment device according to claim 1, wherein the heat insulating coating contains a particle with a heat insulation property.

14. A method of producing the treatment device according to claim 1, the method comprising:
   applying a first resin having a heat insulation property to the treatment portion and baking the first resin to form the heat insulating coating; and
   applying a second resin to at least a surface of the heat insulating coating and baking the second resin to form the resin coating.

15. A treatment device comprising:
   a treatment portion configured to treat biological tissue by supplying at least one type of energy;
   a heat insulating coating provided on the treatment portion; and
   a resin coating provided on the heat insulating coating and on the treatment portion, the resin coating being formed of a different material than the heat insulating coating, wherein the resin coating extends beyond a distal end of the heat insulating coating and seals the distal end of the heat insulating coating.

16. The treatment device according to claim 15, wherein the resin coating seals a proximal end of the heat insulating coating.

17. A method of producing the treatment device according to claim 15, the method comprising:
   applying a first resin having a heat insulation property to the treatment portion and baking the first resin to form the heat insulating coating; and
   applying a second resin to at least a surface of the heat insulating coating and baking the second resin to form the resin coating.

18. A treatment device comprising:
   a treatment portion configured to treat biological tissue by supplying at least one type of energy, wherein the treatment portion includes:
      a first region at a distal end of the treatment portion;
      a second region on a proximal side of the first region, the second region comprising a protection coating made of a resin;
      a third region on a proximal side of the second region, the third region comprising (i) a heat insulating layer having a porous structure, and (ii) the protection coating covering the heat insulating layer; and
      a fourth region on a proximal side of the third region, the fourth region comprising the protection coating,
   wherein the heat insulating layer is included only in the third region.

19. The treatment device according to claim 1, wherein the treatment device is an ultrasonic probe.

20. A method of producing the treatment device according to claim 18, the method comprising:
   applying a first resin having a heat insulation property to the treatment portion and baking the first resin to form the heat insulating layer; and
   applying a second resin to at least a surface of the heat insulating layer and baking the second resin to form the protection coating.

* * * * *